US005705199A

United States Patent [19]

Maish

[11] Patent Number: 5,705,199
[45] Date of Patent: Jan. 6, 1998

[54] ANIMAL CONTROL SUBSTANCE AND METHOD OF USE

[76] Inventor: Bill Maish, P.O. Box 1058, Lake Oswego, Oreg. 97034

[21] Appl. No.: 394,438

[22] Filed: Feb. 24, 1995

[51] Int. Cl.$^6$ .......... A01N 59/00; A01N 59/06; A01N 59/16; A01N 37/02

[52] U.S. Cl. .......... 424/648; 424/84; 424/600; 424/617; 424/646; 424/647; 424/682; 424/690; 424/691; 424/698; 514/553; 514/557; 514/574; 514/918; 514/920

[58] Field of Search .......... 426/1; 424/84, 424/600, 646, 647, 648, 617, 682, 690, 691, 698; 43/124; 514/920, 553, 557, 574, 918

[56] References Cited

U.S. PATENT DOCUMENTS

| | | | |
|---|---|---|---|
| 2,790,744 | 4/1957 | Shearer et al. | 514/920 |
| 4,388,303 | 6/1983 | Allan | 514/920 |
| 4,735,803 | 4/1988 | Katz et al. | 514/920 |
| 5,402,597 | 4/1995 | Lech | 43/124 |
| 5,464,625 | 11/1995 | Nolte et al. | 514/920 |

FOREIGN PATENT DOCUMENTS 61-238707  10/1986  Japan .

OTHER PUBLICATIONS

Chemical Abstracts, vol. 106, 151629v (1987).
The Merck Index, 10th ed., Merck & Co., Inc., NJ, 1983, pp. 283–284.
The Merck Index, 10th ed., Merck & Co., Inc., Rahway (NJ), 1983, p. 582, item 3992.
CRC Handbook of Chemistry and Physics, 59th ed., 1978, CRC Press, Inc., p. B–90, B–127.
Farm Chemicals Handbook '82, Meister Publishing Co., 1982, Willoughby (Ohio), p. B32.

*Primary Examiner*—John Pak
*Attorney, Agent, or Firm*—Robert L. Harrington

[57] ABSTRACT

A substance produced from a combination of acid based ingredients and a mole attracting herb. Placement of the substance into a mole tunnel attracts the mole and upon contact with the substance becomes repelled by the acid taste.

5 Claims, 2 Drawing Sheets

ANIMAL CONTROL SUBSTANCE AND METHOD OF USE

FIELD OF THE INVENTION

This invention relates to a substance that repels small animals such as moles (and, e.g., gophers) and with proper use will expel the animals from a homeowner's yard, from a golf course or other area where the animals create damage and are unwanted.

BACKGROUND OF THE INVENTION

A very common plague to homeowners is the common mole. A mole will dig tunnels under a homeowner's yard and in some unknown pattern digs to the surface and in the process creates unsightful mounds of dirt. A single busy mole can create numerous mounds of dirt in a homeowner's otherwise groomed lawn to the great frustration of the homeowner. Many products have been devised and made available to homeowners to help rid them of the mole or moles from his yard.

The products are typically of two types. One type simply sets about destroying the animal. Traps, poison and even small explosives are used to destroy moles. A more passive and humane product simply attempts to expel the animal from the homeowner's yard. An example of the latter product is a vibrating probe. Supposedly the vibration transmitted into the ground is sensed by the mole and he leaves that area.

Poisons, traps and explosives are strongly resisted by homeowners particularly because of the danger to children and pets. Most homeowners simply want the moles to disappear from their yard. In any event, the mole is extremely sensitive and great care has to be taken to avoid leaving human scent on any of the products used as the mole will simply avoid the product while still going about his tunnel digging activities. The vibrating probe at best is limited to a small area of the yard and numerous probes have to be installed to achieve expulsion of a mole from a typical yard.

BRIEF DESCRIPTION OF THE PRESENT INVENTION

The preferred embodiment of the present invention can be considered to rely on a form of shock treatment. A substance is prepared that consists of three primary ingredients. One ingredient attracts the mole. Typically this ingredient is a form of vegetation. Thus, when the substance is inserted in the ground, e.g., in the mole's tunnel, the mole's highly sensitive smell will draw the mole to the substance. The second and third ingredients are both mildly acidic. The combination of ingredients is quite harmless to either children or pets. One of the ingredients includes metal ions that dissolve in water and has a pH of about 3 and the other material includes hydrogen ions that are released when dissolved in water with a pH of about 4 to 4.5. When moistened, the two ingredients combine to form an acidic material having a pH of about 2. The moistened substance is comparable in pH, for example, to lemon juice. A layman (in chemical terminology) doesn't think of lemon juice as being acidic but he does think of it as being very tart. A taste of undiluted lemon juice will likely be a one time experience as the tart or sour taste is not pleasant. It is theorized that the combination of ingredients when inserted into the ground, absorbs ground moisture and converts to the enhanced acidity. The acid based ingredients are selected to be substantially odorless (the acid doesn't vaporize in water) and thus the animal is not repelled by the acid smell. The vegetation ingredient attracts the mole and the mole contacts the substance and may even eat some of it. The mole's sensors (whiskers, nose, teeth, paws, tongue) are jolted by the acidic taste and feel and it simply vacates that area. The substance is non-toxic and the affect of the acidic taste and feel wears off in time without permanent injury to the mole.

Whereas the above is largely theory, it is based on a study of the animal habits over a long period of time. Moles are blind and rely on highly sensitive feelers and inherent sense of direction and location. They relate to unpleasant experiences and steer a wide path around an area where they have been subjected to an unpleasant experience. Tests have been conducted based on the above theory with immediate success. Yards have been treated with the substance and following treatment, the moles disappear. Different schemes have been developed for using the substance and in certain instances, the moles have in effect been herded into traps. Whereas traps normally carry human scent and are avoided by the moles, it is theorized that the acidic taste and/or feel dulls the mole's senses and it can't sense the human scent for a period of time after contacting the substance. The substance is low cost and made even lower in cost by mixing the substance with a large quantity of sand. The sand aids in pouring the substance out of a container and into the mole's tunnel.

The invention will be more fully appreciated and understood with reference to the following detailed description and drawings.

DESCRIPTION OF THE PREFERRED EMBODIMENT

Figure 1:
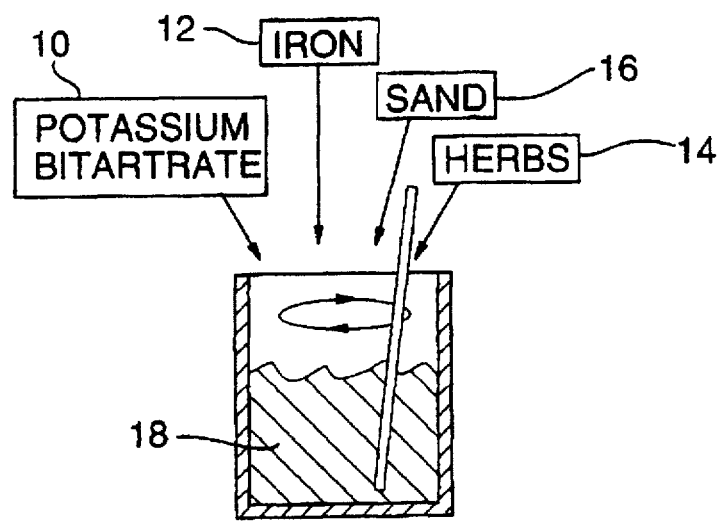
FIG. 1 is a schematic illustration of the process of intermixing measured quantities of three ingredients to make up the substance of the present invention.

With reference to FIG. 1, ingredient 10 is a bitartrate or bioxalate. It has in its molecular makeup a hydrogen ion that is readily released to water. It is non-toxic and has a pH preferably in the range of about 4–4.5 pH. A very small quantity of the mixture is made up of the bitartrate. A specific example of the ingredient used is cream of tartar (potassium bitritrate) or bioxilate. Other ingredients that can be substituted for ingredient 10 are known to those skilled in the art.

Ingredient 12 is used in much greater quantity, e.g., about five parts ingredient 10 to 3,000 parts ingredient 12. Ingredient 12 is a metal ion that dissolves in water and has a pH of about 3. It is non-toxic. Iron is preferred but other metal ions can be used, e.g., aluminum and other materials which are known to the art. An iron ingredient used by applicant is Ferrous Sulfate Monohydrate (chemical name), manufactured by Fugi Titanium Industry Co., Ltd. and distributed by Hydro Agri of San Francisco, Calif. The product is sold, e.g., as a soil enhancer (fertilizer) through agricultural product stores.

The third ingredient 14 is any product that attracts the animal. It has been determined that moles are fond of herbs such as thyme, sage, fennel, basil, lavender, maryann and rosemary. As explained, the function of this third ingredient, which is a form of vegetation and preferably an herb, is to attract the animal. Only a small amount of any of the ingredients that are listed is required, e.g., less than 1% of the substance being ingredient 14. It is considered important not to use so much as to provide an overpowering smell as a mole has a very sensitive smelling ability. The mixture can, of course, be varied over a considerable range and the amount may vary depending on the form of the ingredient.

A fourth ingredient 16 is considered to function merely as the carrier of ingredients 10, 12 and 14. Sand is ideal in that the other three mixtures can be homogeneously mixed with the loose sand, moisture readily penetrates through the sand, sand pours easily, and it contains no characteristics that detrimentally affects the acidity of ingredients 10 or 12 or the taste/smell of ingredient 14. Again the amount may vary but ideally it has been found that the sand should make up about 70% of the mixture/substance, e.g., 6,994 parts sand to 3,000 parts iron to five parts potassium bitartrate to one part herb. The four ingredients are mixed (schematically illustrated by the swirling action of the ingredients) and the substantially homogenous mixture becomes substance 18.

Figure 2:
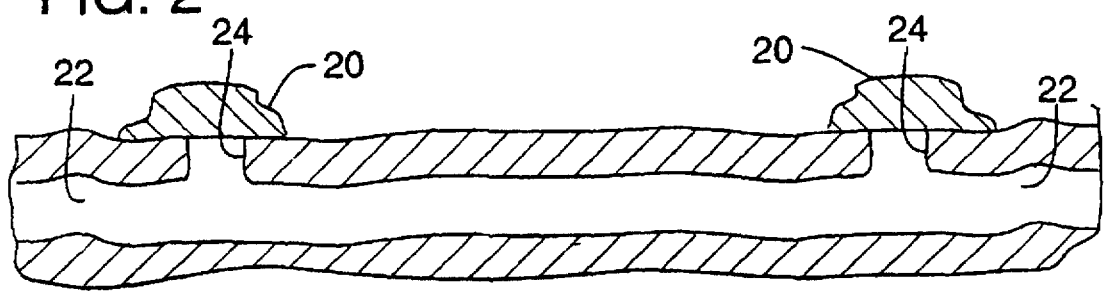
FIGS. 2A–2D schematically illustrates the steps used in applying the substance of FIG. 1 to a mole tunnel.
Figure 2B:
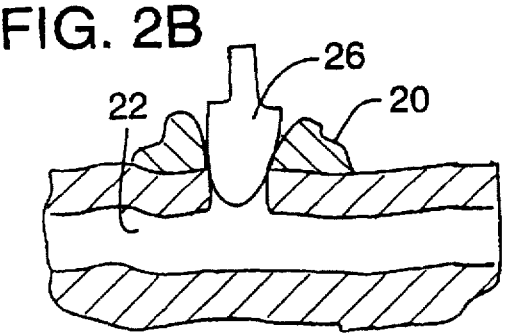
Figure 2C:
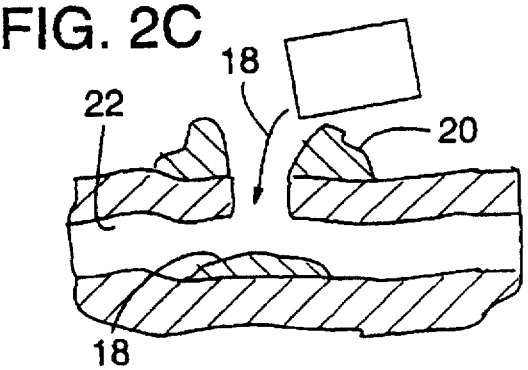

Reference is now made to FIGS. 2A–2D which illustrate the process for use of the substance 18 of FIG. 1. FIG. 2A represents a plurality of mole hills 20 which is no more than a pile of dirt that has been pushed to the surface from the mole's tunnel 22 (channel 24 being a "mole hole" which has been formed by a mole through which the dirt is pushed). The home owner (gardener, lawn keeper, etc.) first locates the mole hole 24, e.g., by poking down through the mole hill with a garden trowel 26 or the like. He then opens the hole sufficiently to enable him to pour a substantial quantity of the substance 18 down through the hole and into the mole's tunnel 22 as illustrated in FIG. 2C. It is suggested that the container be first shaken to insure that the ingredients are properly mixed.

Figure 2D:
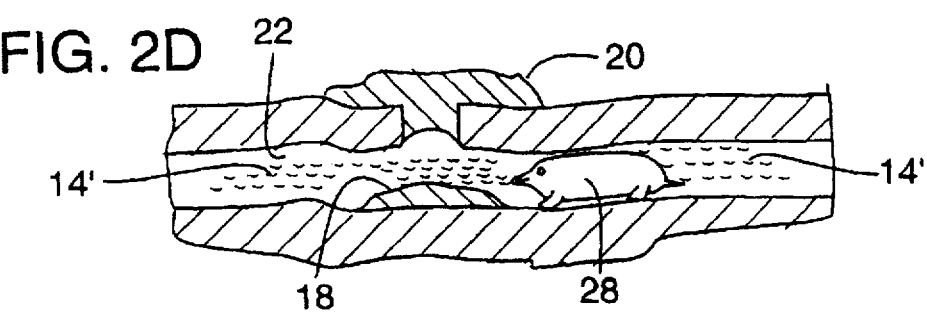

After the substance 18 is poured into the tunnel, the mole hill is pushed down, e.g., stepped down, to block the mole tunnel 22 and close the mole hole 24. This is illustrated in FIG. 2D. Not illustrated is the conversion of the ingredients 10 and 12 in the substance after it is deposited into the tunnel. Even a small amount of moisture that is present in the tunnel (in the ground and in the air) will be absorbed by the ingredients 10 and 12 of the substance and they will inter-react. The inter-reaction of the ingredients enhances the acidity which is believed to be about pH 2.

The odor of the ingredient 14 (14') attracts the mole 26 who then starts digging through the material blocking the tunnel to get at the herbs of ingredient 14. As the mole commences digging, it comes into contact with the enhanced mixture of ingredients 10 and 12. Whereas the pungent/tart taste of the acid is distasteful to the human sense, the mole is believed to be more highly affected and the result is one of shock to the mole. The mole's reaction is to leave the area and not return any time in the near future.

Figure 3A:
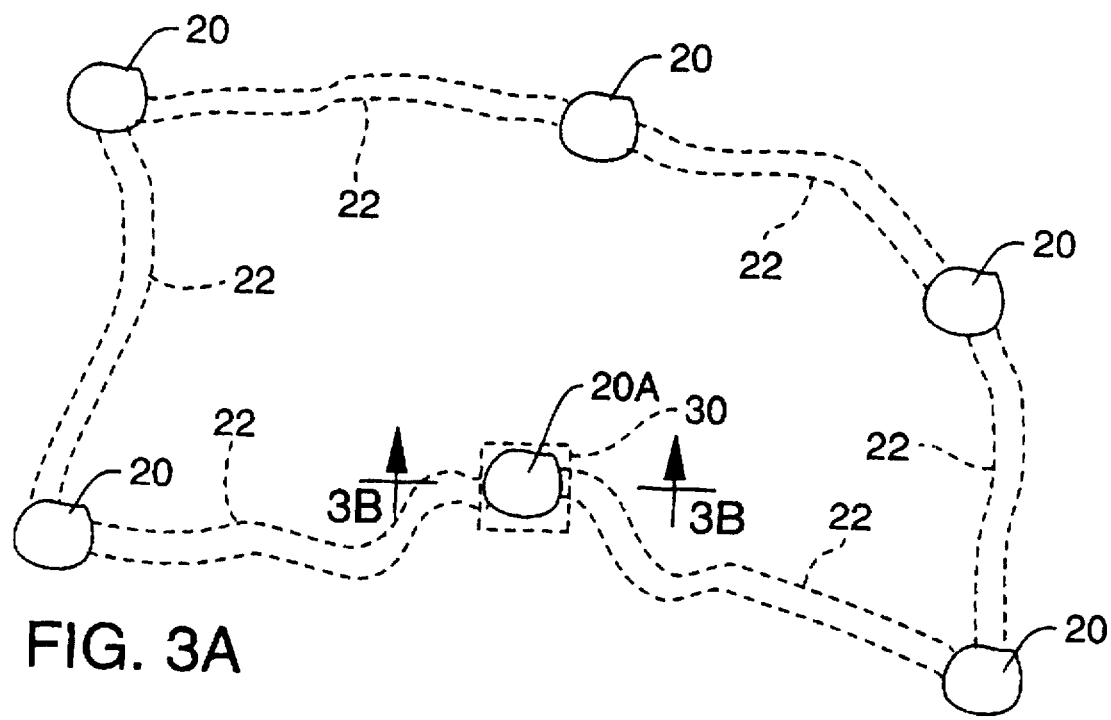
FIGS. 3A and 3B illustrate an alternate method for treating a mole infested yard.
Figure 3B:
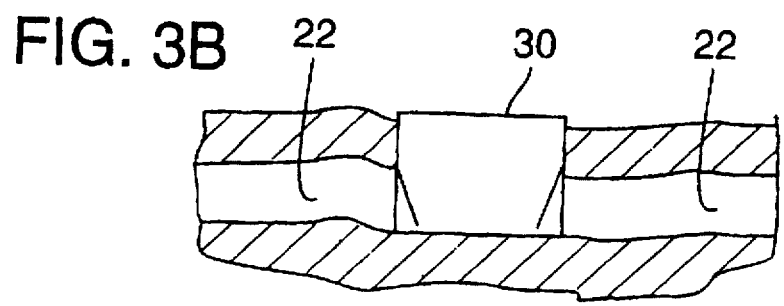

FIG. 3A illustrates an alternative procedure. There are occasions where the land owner needs to get rid of the moles rather than simply repel them. FIG. 3A illustrates a pattern of mole hills and tunnels as may be present, e.g., on a golf course. Whereas the groomed lawn of a golf course extends over many acres, simply repelling the moles may involve merely sending them from one area to another and then to another, etc. all on the golf course.

Whereas trapping is not normally successful, it has been found that the substance of the present invention can be used to "herd" a mole or moles into a trap. Consider a pattern such as illustrated in FIG. 3A where mole hills 20 are spread over a wide area. An assumption can be made that they are interconnected by mole tunnels 22. A central mole hill 20a in the pattern of mole hills 20 is selected and a trap 30 is installed in the ground (in the path of the mole tunnel) at that location. The outlying mole hills are treated as explained for FIGS. 2A–2D. It is believed that the substance when contacted by the moles dulls the mole's senses and in his rapid retreat from the treated mole hills he is oblivious to the human scent of the trap. In tests performed, this trapping process has been found very successful.

Whereas moles have been a problem to lawn grooming for decades and whereas many attempts have been made to provide a product that will get rid of them, no one is believed to have employed a harmless acid substance that attacks the mole's sensitive sensors (taste, smell, feel (e.g., teeth)). The invention is not limited to the specific ingredients identified in the examples presented above nor is it limited to the specific treatment steps. It is believed important to combine an ingredient that is attractive to the animal with the acid. It is furthermore desirable to use a combination of acid materials that inter-react in the presence of water (moisture) to produce a strong acid taste and feel but with minimal or no smell so as to leave the dominant but subtle smell of the herb ingredient. With this understanding, persons skilled in the art will be aware of a number of substitute or alternative ingredients for each of the ingredients of the above sample. Thus, the invention is defined broadly as set forth in the claims appended hereto.

I claim:

1. A substance for underground application to repel small animals from a lawn area, comprising:

a combination of ingredients including:

a) a material having as its base ingredient a non-toxic metal based ion that readily dissolves in water and does not vaporize;

b) a material having a hydrogen ion that is readily released in water selected from the group consisting of bioxalate and bitartrate;

said ingredients a) and b) inter-reacting in the presence of water to enhance the acidity without becoming toxic;

c) a vegetation that emits a smell that is attractive to the small animal to be repelled; and d) a quantity of soil as a carrier, the amount being at least greater than the combined quantities of a), b) and c);

said ingredients a), b), c) and d) homogeneously mixed together as a safe non-toxic lawn treatment to be inserted underground and reacting with ground moisture to enhance the acidity of the substance for shocking the senses of the animal on contact.

2. A substance as defined in claim 1 wherein ingredient d) is sand.

3. A substance as defined in claim 1 wherein ingredient a) has a pH of about 3 and ingredient b) has a pH of about 4–4.5.

4. A substance as defined in claim 1 wherein ingredient a) is ferrous sulfate monohydrate and ingredient b) is potassium bitartrate.

5. A method of expelling moles from a yard area which comprises:

a) obtaining a substance as defined in claim 1;

b) locating a mole hill in a yard area;

c) inserting the substance of a) through the mole hill and into an underlying mole tunnel;

d) causing the substance to become moistened to enhance the acidity; and e) said vegetation of substance a) attracting moles and upon contact repelling the moles as a result of the mole's sensitivity to the enhanced acidity.

\* \* \* \* \*